(12) United States Patent
Hirahara

(10) Patent No.: US 10,040,070 B2
(45) Date of Patent: Aug. 7, 2018

(54) PCR DEVICE AND PCR METHOD

(71) Applicant: Fluid Incorporated, Yokohama-shi (JP)

(72) Inventor: Shuzo Hirahara, Yokohama (JP)

(73) Assignee: Fluid Incorporated, Yokohama-shi (JP)

( * ) Notice: Subject to any disclaimer, the term of this patent is extended or adjusted under 35 U.S.C. 154(b) by 224 days.

(21) Appl. No.: 15/002,715

(22) Filed: Jan. 21, 2016

(65) Prior Publication Data

US 2016/0214111 A1 Jul. 28, 2016

(30) Foreign Application Priority Data

Jan. 22, 2015 (JP) ................................. 2015-009891

(51) Int. Cl.
| | | |
|---|---|---|
| *C12P 19/34* | (2006.01) | |
| *C12M 1/00* | (2006.01) | |
| *B01L 7/00* | (2006.01) | |
| *B01L 3/00* | (2006.01) | |
| *F04B 19/00* | (2006.01) | |
| *C12Q 1/686* | (2018.01) | |

(52) U.S. Cl.
CPC .............. *B01L 7/52* (2013.01); *B01L 3/5027* (2013.01); *B01L 7/525* (2013.01); *F04B 19/006* (2013.01); *B01L 2200/14* (2013.01); *B01L 2300/088* (2013.01); *B01L 2300/0816* (2013.01); *B01L 2300/1833* (2013.01); *C12Q 1/686* (2013.01)

(58) Field of Classification Search
CPC ......... B01L 2200/14; B01L 2300/0816; B01L 2300/088; B01L 2300/1833; B01L 3/5027; B01L 7/52; B01L 7/525; C12Q 1/686; F04B 19/006

USPC ................................. 435/283.1, 981.2, 91.2
See application file for complete search history.

(56) References Cited

U.S. PATENT DOCUMENTS

| | | |
|---|---|---|
| 2010/0267127 A1 | 10/2010 | Chung et al. |
| 2011/0212492 A1 | 9/2011 | Hirahara |
| 2014/0141498 A1 | 5/2014 | Enzelberger et al. |

FOREIGN PATENT DOCUMENTS

| | | |
|---|---|---|
| EP | 1972374 A2 | 9/2008 |
| EP | 2322647 A2 | 5/2011 |
| JP | 08-322569 A | 12/1996 |
| JP | 2001-169733 A | 6/2001 |
| JP | 2001-521622 A | 11/2001 |
| JP | 2002-218958 A | 8/2002 |
| JP | 2002-238523 A | 8/2002 |
| JP | 2009-529909 A | 8/2009 |
| JP | 2011-115159 A | 6/2011 |
| WO | WO-98/45481 A1 | 10/1998 |
| WO | WO-2007-107947 A1 | 9/2007 |

OTHER PUBLICATIONS

Office Action dated Mar. 18, 2015, issued for the Japanese patent application No. 2015-009891 and an English abstract thereof.
Extended European Search Report dated Jun. 1, 2016, issued for the European patent application No. 16152303.0.

*Primary Examiner* — Cynthia B Wilder
(74) *Attorney, Agent, or Firm* — Locke Lord LLP

(57) ABSTRACT

A reaction container 10 of the PCR device 1 has a tubular ring channel 20 formed by a substrate 11, a channel forming plate 12, and a cover plate 13. The ring channel 20 comprises an electrode pair 21 disposed, in a diametrical direction of an inner surface of one side wall of the ring channel 20, to face each other with a horizontal gap interposed therebetween, and is vertically erected. The gap length of the electrode pair 21 is across the entire width within a cross-section of the ring channel 20.

4 Claims, 5 Drawing Sheets

PCR DEVICE AND PCR METHOD

TECHNICAL FIELD

The present invention relates to a PCR (Polymerase Chain Reaction) device and a PCR method, and particularly, to a PCR device and a PCR method that achieve a reduction in volume and even heating of a channel.

BACKGROUND ART

Because a conventional PCR method using Joule heating of a reaction solution makes a DC current flow through the reaction solution, the reaction solution is electrolyzed to produce unnecessary gas on the periphery of the electrodes, and produce unnecessary acidic and alkaline solutions. Moreover, because a voltage is applied to both ends of a long channel, a high voltage must be applied to generate necessary Joule heat, causing a large circuit burden.

Therefore, for example, Patent Literature 1 describes a PCR device for which, on an inner surface of a container to carry out polymerase chain reaction (PCR), an electrode pair to be disposed to face each other with a gap along a flow of a reaction solution interposed therebetween, and which applies an AC voltage to the electrode pair to make an AC current flow through the reaction solution, thereby generating Joule heat to control the reaction solution in temperature.

FIG. 6 is a front view of a reaction container of the PCR device described in Patent Literature 1.

As depicted in FIG. 6, the PCR device described in Patent Literature 1 comprises a cover plate 41, an outlet 42, an inlet 43, a channel 44, an electrode pair 45, a channel forming plate 46, and a substrate, and the reaction container is vertically erected. The PCR device described in Patent Literature 1 makes an electric current flow into a reaction solution in a gap between the electrode pair 45, and heats the reaction solution by Joule heat thereof to cause PCR amplification. The reaction solution is, by circulating in the annular channel 44, raised and lowered in temperature to undergo temperature changes of a PCR cycle so as to cause PCR amplification.

CITATION LIST

Patent Literature

[Patent Literature 1] JP 2011-115159 A (FIG. 4)

SUMMARY OF INVENTION

Technical Problem

However, the PCR device described in Patent Literature 1 has a linear part in the annular channel 44, which thus hinders downsizing, making a reduction in channel volume difficult.

Moreover, because the electrode pair 45 is long and narrow, a high manufacturing accuracy is necessary. Moreover, because the gap of the electrode pair 45 through which an electric current flows is only in the middle within a channel cross-section, only the middle within the cross-section corresponds to apart to be heated, causing a temperature unevenness.

In view of the above problems, it is an object of the present invention to provide a PCR device and a PCR method capable of achieving a reduction in size and volume and even heating of a channel.

Solution to Problem

A PCR device according to the present invention comprises an annular container, a flow path cross-section of which is rectangular, which is in a circular annular shape as a whole and disposed by vertical installation, to carry out polymerase chain reaction (PCR); an electrode pair consisting of two electrodes disposed on one inner surface of opposed substrates to form the annular container, disposed to face each other with a gap interposed therebetween, said gap extending across an entire width of a flow of a reaction solution, intersecting the flow, and having a horizontal gap center line; and a control unit which applies an AC voltage to the electrode pair to make an AC current flow through the reaction solution, thereby generating Joule heat to make the reaction solution flow upward and control the reaction solution in temperature.

Moreover, a PCR device according to the present invention comprises an annular container, a flow path cross-section of which is rectangular, which is in a circular annular shape as a whole and disposed by vertical installation, to carry out polymerase chain reaction (PCR); an electrode pair consisting of electrodes each of which is disposed on respective inner surfaces of opposed substrates to form the annular container, disposed to face each other with a gap interposed therebetween, said gap extending across an entire width of a flow of a reaction solution, intersecting the flow, and having a horizontal gap center line; and a control unit which applies an AC voltage to the electrode pair to make an AC current flow through the reaction solution, thereby generating Joule heat to make the reaction solution flow upward and control the reaction solution in temperature.

A PCR method according to the present invention provides an electrode pair consisting of two electrodes disposed on one inner surface of opposed substrates to form an annular container, a flow path cross-section of which is rectangular, and which is in a circular annular shape as a whole and disposed by vertical installation, to carry out polymerase chain reaction (PCR), and disposed to face each other with a gap interposed therebetween, said gap extending across an entire width of a flow of a reaction solution, intersecting the flow, and having a horizontal gap center line, and applies an AC voltage to the electrode pair to make an AC current flow through the reaction solution, thereby generating Joule heat to make the reaction solution flow upward and control the reaction solution in temperature.

Moreover, a PCR method according to the present invention provides an electrode pair consisting of electrodes each of which is disposed on respective inner surfaces of opposed substrates to form the annular container, a flow path cross-section of which is rectangular, and which is in a circular annular shape as a whole and disposed by vertical installation, to carry out polymerase chain reaction (PCR), and disposed to face each other with a gap interposed therebetween, said gap extending across an entire width of a flow of a reaction solution, intersecting the flow, and having a horizontal gap center line, and applies an AC voltage to the electrode pair to make an AC current flow through the reaction solution, thereby generating Joule heat to make the reaction solution flow upward and control the reaction solution in temperature.

Moreover, the electrode pair, as a result of consisting of two electrodes disposed on one of the opposed substrates to form the annular container, suffices with forming electrodes on only one substrate, thus allowing a reduction in manufacturing cost.

Moreover, the electrode pair, as a result of consisting of two electrodes disposed on one each of the opposed substrates to form the annular container, allows even heating in not only a width direction but also a depth direction of the annular container.

Advantageous Effects of Invention

The present invention realizes a PCR device and a PCR method capable of achieving a reduction in size and volume and even heating of a channel.

DESCRIPTION OF EMBODIMENTS

Hereinafter, modes for carrying out the present invention will be described in detail with reference to the accompanying drawings.

Example 1

Figure 1:
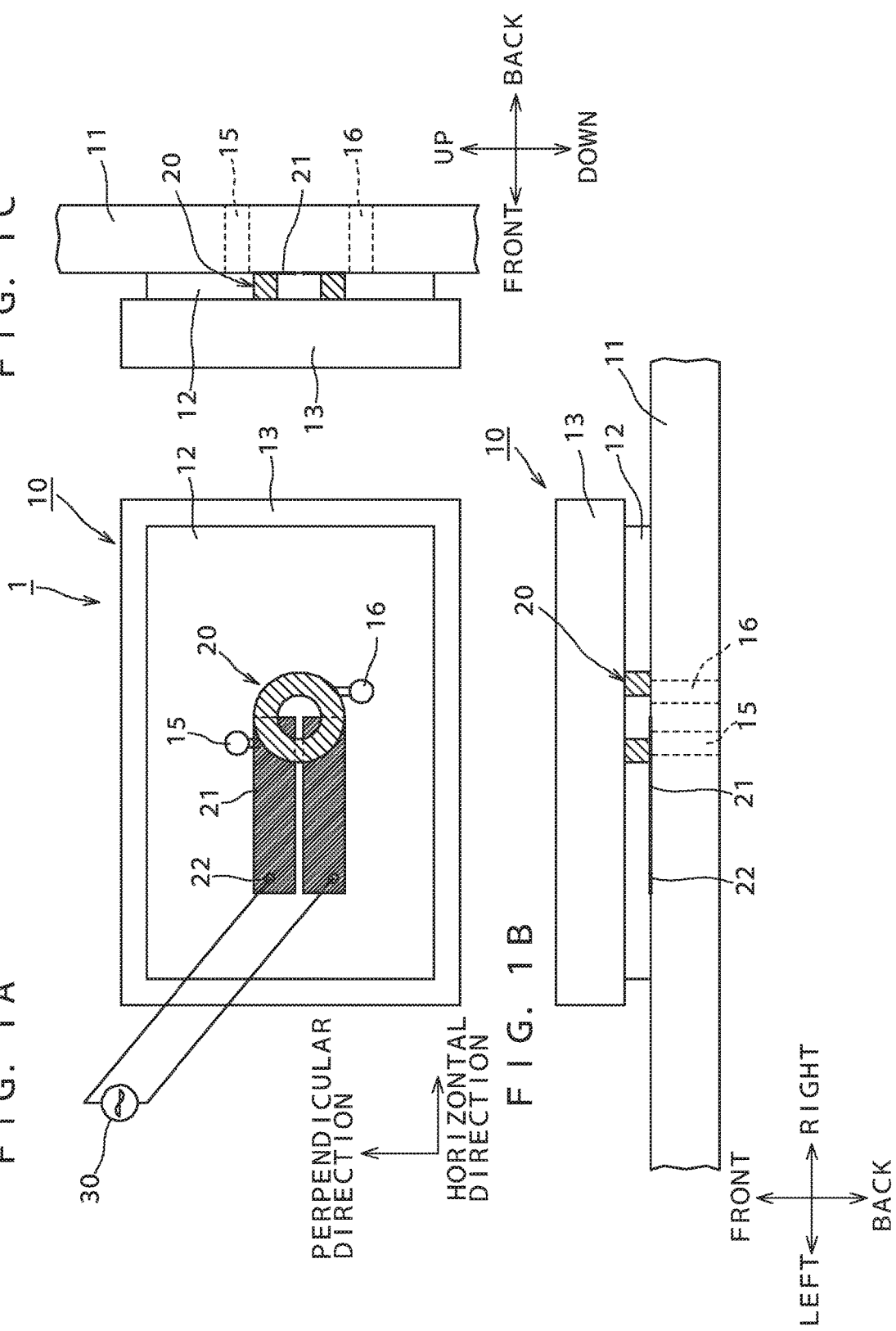
FIG. 1A to FIG. 1C are views depicting a configuration of a reaction container of a PCR device according to Example 1 of the present invention.

FIG. 1A to FIG. 1C are views depicting a configuration of a reaction container of a PCR device according to Example 1 of the present invention, FIG. 1A is its front view, FIG. 1B is its bottom view, and FIG. 1C is its side view.

Figure 2:
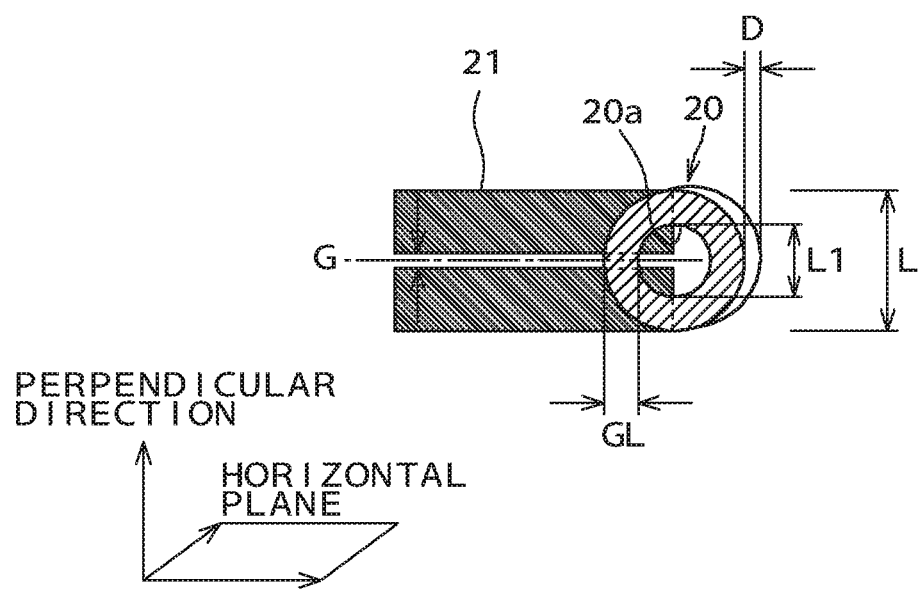
FIG. 2 is a perspective view depicting a ring channel and an electrode pair of the reaction container of the PCR device according to Example 1 of the present invention.

On the other hand, FIG. 2 is a perspective view depicting a ring channel 20 and an electrode pair 21. Additionally, in examples of the present invention, "up" or "upper" denotes a vertically upper side, "down" or "lower" denotes a vertically lower side, "horizontal" or a "horizontal direction" denotes a direction orthogonal to a vertical direction. Moreover, "front" means a near side direction when viewed from the front, "back" means a back direction when viewed from the front, "left" means a left direction when viewed from the front, "right" means a right direction when viewed from the front, and "perpendicular" means a vertical direction orthogonal to the horizontal direction.

First, description will be given of a configuration of the PCR device.

As depicted in FIG. 1A to FIG. 1C, the reaction container 10 (annular container) of the PCR device 1 comprises a substrate 11, a channel forming plate 12, and a cover plate 13. The substrate 11, the channel forming plate 12, and the cover plate 13 form an annular tubular ring channel 20. The ring channel 20 has an annular shape, and is, for example, a circular annular-shaped chamber.

As depicted in FIG. 2, the ring channel 20 is disposed by vertical installation such that its diametrical direction stands up perpendicularly with respect to a horizontal plane. The ring channel 20 has an outer diameter L of, preferably, 1 mm to 3 mm, and of, for example, 2 mm. Moreover, the ring channel 20 includes a circular opening portion 20a, and the ring channel 20 has an inner diameter L1 of, preferably, 0.5 mm to 1.5 mm, and of, for example, 1 mm. That is, the ring channel 20 is a circular annular chamber having a flow path between the outer diameter of 2 mm and the inner diameter of 1 mm, for example. Additionally, in the present example, because a center point of the ring channel 20 is made to coincide with a center point of the circular opening portion 20a, the flow path between the outer diameter and the inner diameter of the ring channel 20 is equal in width across the entire circumference. The center points may be slightly misaligned. The ring channel 20 has a flow path depth D of, preferably, 100 μm to 300 μm, and of, for example, 200 μm, which is determined by a thickness of the channel forming plate 12. Moreover, the ring channel 20 has a flow path volume of, preferably, 0.3 μL to 1.0 μL, and of, for example, 0.47 μL. In this case, a flow path cross-section is in a rectangular shape of 500 μm×200 μm.

The substrate 11 depicted in FIG. 1A to FIG. 1C is made of glass, and patterned on an upper surface thereof with an electrode pair 21 prepared by evaporating thin chrome and thereon gold, and the electrode pair 21 has leader electrode portions 22 extracted therefrom to an outer circumference side of the ring channel 20. The electrode pair 21 and the leader electrode portions 22 are formed by evaporating gold, and their film thickness is extremely thin so as to be almost negligible. Therefore, a reaction solution is not obstructed from flowing even if there is formed an electrode pair 21 on the substrate 11.

As depicted in FIG. 1A to FIG. 1C and FIG. 2, the electrode pair 21 has a gap width G of, preferably, 10 μm to 500 μm, and of, for example, 100 μm, and has a gap length GL of, preferably, 0.25 mm to 1 mm, and of, for example, 0.5 mm. The leader electrode portions 22 are, for example, 4 mm long. As depicted in FIG. 2, the ring channel 20 is disposed such that its diametrical direction stands up perpendicularly, and the electrode pair 21 is disposed at least either the left or right of the ring channel 20. Moreover, a center line (refer to the alternate long and short dashed line in FIG. 2) of the gap of the electrode pair 21 is in the horizontal direction. In this example, the gap of the electrode pair 21 horizontally crosses the ring channel 20 in the left side of the ring channel 20. The reaction solution is subjected to Joule heating by the electrode pair 21 to reach a denaturation temperature, and made into an upward flow in the periphery of the electrode pair 21. In this case, a reaction solution flow is upward at the position of the gap of the electrode pair 21 in the left side of the ring channel 20. The reaction solution is thereby made to flow upward in a direction to intersect the center line of the gap of the electrode pair 21 so as to circulate the reaction solution within the annular ring channel 20.

As above, the ring channel 20 can make the reaction solution flow upward in a direction to intersect the center line (refer to the alternate long and short dashed line in FIG. 2) of the gap of the electrode pair 21, which is horizontal, so as to circulate the reaction solution within the annular ring channel 20.

In the present example, because the gap of the electrode pair 21 horizontally crosses the ring channel 20, a heating region is small, and heating power is small accordingly, however, because the ring channel 20 itself is small and therefore a small amount of reaction solution flows within the ring channel 20, a PCR cycle can be sufficiently realized. Moreover, because the gap length GL of the electrode pair 21 is across the entire width within a channel cross-section, the whole cross-section of a flowing solution can be heated.

The channel forming plate 12 is made of PDMS (polydimethylsiloxane), and disposed by being bonded on the substrate 11. The channel forming plate 12 has a function as a spacer to keep a predetermined distance between the substrate 11 and the cover plate 13, and its thickness (for example, 200 µm) corresponds to the flow path depth D of the ring channel 20. The channel forming plate 12 is provided with an annular groove to form the ring channel 20. Moreover, an inlet well 15 of a reaction solution is provided on the side of the electrode pair 21 of an upper end of the annular groove, and on the side to separate from the electrode pair 21 of a lower end, an outlet well 16 of the reaction solution is provided.

The cover plate 13 is made of glass, and forms the ring channel 20 by covering the entire surface of the channel forming plate 12.

Through-holes (not depicted) are opened in the thickness direction at parts of the substrate 11 being in contact with the inlet well 15 and the outlet well 16 provided at the upper and lower ends of the ring channel 20, and tubes (not depicted) are connected to these through-holes to let the reaction solution flow in and out.

A control section 30 (control unit) applies an AC voltage necessary for performing a PCR cycle to the electrode pair 21. The AC has a frequency of 10 kHz to 10 MHz, for example, 1 MHz. As compared with a slight amount of reaction solution within the ring channel 20, large electrodes can be used, and a configuration for directly heating the reaction solution is adopted, and thus a time constant of a response of the reaction solution temperature to voltage application can be provided within 1 second.

In the following, operation of the PCR device configured as described above will be described.

As PCR cycles, for example, the following steps are repeatedly performed 20 to 30 cycles in order.
(1) 2 seconds to 10 seconds of denaturation ($\approx$94° C.)
(2) 5 seconds of annealing (54° C. to 66° C.)
(3) 5 seconds to 15 seconds of extension ($\approx$/2° C.)

In actuality, as a PCR cycle of two steps in which annealing and extension are performed at the same temperature, an environment surrounding the reaction container 10 is maintained at the annealing/extension temperature, and a corresponding AC voltage is applied to the electrode pair 21 in order to reach the denaturation temperature. An AC current is thereby made to flow through the reaction solution to control the reaction solution in temperature by heating the reaction solution by Joule heat, so as to perform a PCR cycle.

In the present example, because an AC current is made to flow through the reaction solution, the AC current does not electrolyze the reaction solution. Moreover, because an electric current is made to flow through the gap of the electrode pair 21, the electric current that flows through the gap is short in distance and a load resistance is therefore small, and thus even with a low application voltage, Joule heat sufficient for temperature control of a PCR cycle can be generated.

Further, when the ring channel 20 of the present example is used, as online processing, linkage with a previous stage or subsequent stage of processing is possible. As the previous stage, grinding of cells, extraction and purification of genes, fragmentation of cells, or the like is feasible, while as the subsequent stage, an electrophoresis analysis, a microarray analysis, or a connection to a mass spectrometer is feasible, and further various gene analysis methods can be linked as an integrated device that is connected directly at a microchannel without a tube.

The PCR device 1 can be constructed as a real-time PCR device using a dye that emits fluorescence by intercalation specifically into double-stranded DNA. A real-time PCR method allows monitoring the amount of PCR amplification in real time for analysis, does not need electrophoresis, and is excellent in promptness and quantitative performance.

Next, description will be given of the PCR method of the present example.

As depicted in FIG. 1A and FIG. 1C, the reaction container 10 of the PCR device 1 is installed in a vertically erected manner.

A reaction solution is injected through the inlet well 15, and discharged through the outlet well 16. The reaction solution is subjected to Joule heating by the electrode pair 21 to reach a denaturation temperature, and made into an upward flow in the periphery of the electrode pair 21 to circulate within the ring channel 20 so as to perform a PCR cycle. A two-step PCR cycle is assumed here. When the PCR is completed, the reaction solution is discharged through the outlet well 16. In addition, the injection and discharge of a reaction solution into and from the reaction container 10 is performed by an external pump or syringe, which is not illustrated.

As depicted in FIG. 2, in the reaction container 10, the electrode pair 21 is disposed either the left or right (in this example, the left side) of the ring channel 20, and the center line of the gap of the electrode pair 21 is disposed so as to lie in the horizontal direction of the ring channel 20. Due to this configuration, the gap of the electrode pair 21 horizontally crosses the ring channel 20 in one left or right side of the ring channel 20.

The ring channel 20 is filled inside with a reaction solution, and an electric current flows into the reaction solution at the gap of the electrode pair 21. Joule heat is then generated by resistance of the reaction solution to heat the reaction solution, so that the reaction solution loses weight to flow upward (a "pump function by heating"). The reaction solution thereby circulates within the channel (in this case, it circulates clockwise). Simultaneously, the reaction solution inside the ring channel 20 is raised in temperature, and is lowered in temperature by circulating and moving to a non-heat generating part. Said reaction solution can, by undergoing temperature changes and making the same into temperature changes for a PCR cycle, cause PCR amplification.

Although this is not illustrated, the ring channel 20 as a whole is controlled in most parts separately by a heater to be a constant temperature (annealing/extension temperature). A reaction solution flow thus flows along the circular shape of the ring channel 20, and the gap of the electrode pair 21 horizontally crosses the ring channel 20 in either the left or right (in this example, the left side) of the ring channel 20. In addition, the "horizontal" described in the present example connotes a horizontal state of being nearly horizontal and with a slight inclination at a level that the above-described "pump function by heating" can be realized, besides literally being horizontal that is orthogonal to the vertical direction.

As depicted in FIG. 2, at the position of the gap of the electrode pair 21 in the left side of the ring channel 20, a reaction solution flow is upward, so that the gap of the electrode pair 21 crosses the reaction solution flow, that is, extends across the entire flow width of the flow path. The electrode pair 21 and the leader electrode portions 22 are evaporated on the substrate 11, and do not obstruct a reaction solution flow because their thickness is 1 μm or less.

As has been described above, the reaction container 10 of the PCR device 1 according to the present example has the tubular ring channel 20 formed by the substrate 11, the channel forming plate 12, and the cover plate 13. The ring channel 20 comprises the electrode pair 21 disposed on an inner surface of one side wall of the ring channel 20 and to face each other with a gap interposed therebetween, the gap being provided in one of the two cross-sections where the ring channel 20 intersects a horizontal plane, and the ring channel 20 is vertically erected. The gap length of the electrode pair 21 is across the entire width within a cross-section of the ring channel 20. The control section 30 applies an AC voltage to the electrode pair 21 to make an AC current flow through a reaction solution, thereby generating Joule heat to control the reaction solution in temperature.

The PCR device 1 and the PCR method according to the present example can thereby obtain the following effects.

Figure 6:
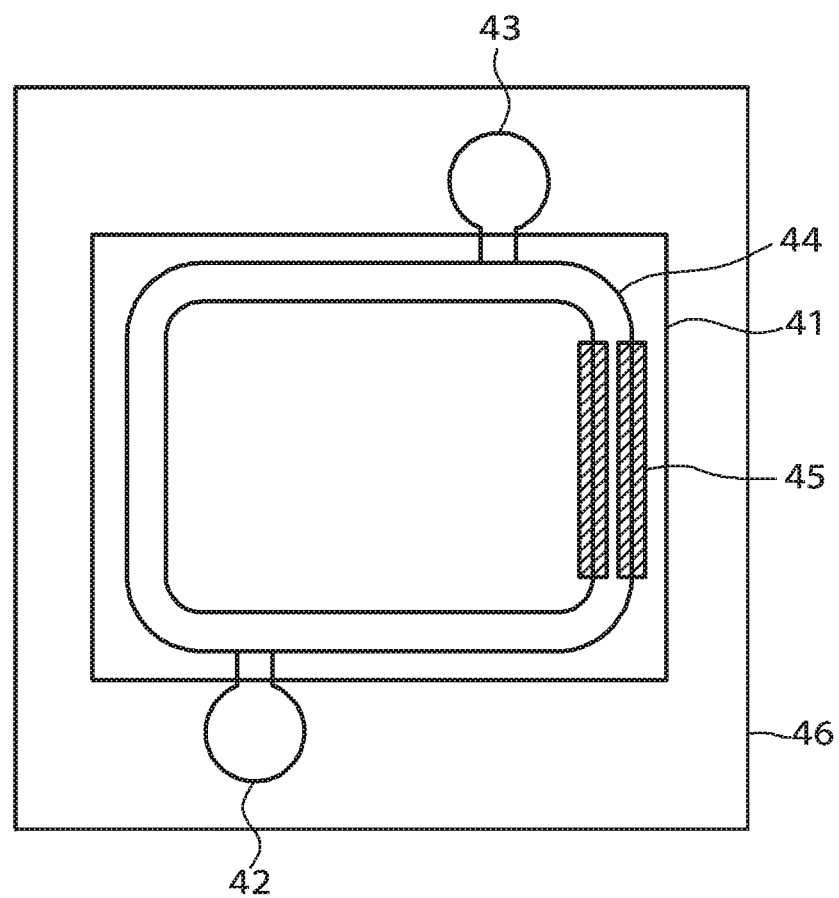
FIG. 6 is a front view of a reaction container of a PCR device of a conventional example.

That is, because the PCR device (refer to FIG. 6) of the conventional example has had a configuration in which a gap between the electrode pair 45 is provided along the channel 44, the channel 44 has required a linear part having a predetermined length, and has thus been in a quadrangular shape despite being an annular shape. Because the channel 44 has the linear part, it has been difficult to reduce the channel 44 in size.

In contrast thereto, the PCR device 1 according to the present example adopts a configuration of, as depicted in FIG. 1A to FIG. 1C and FIG. 2, disposing the gap of the electrode pair 21 so as to cross one side of the circular annular shape of the ring channel 20. Thus, the ring channel 20 no longer requires a linear part as in the conventional example, can make a reaction solution flow smoothly within the circular annular shape, and the overall size of the ring channel 20 can be reduced. Because of the downsizing of the ring channel 20, PCR amplification can be performed by a smaller amount of reaction solution.

Moreover, in the conventional example, the electrode pair 45 (refer to FIG. 6) is long and narrow, so that a high manufacturing accuracy is thus necessary, and because the gap of the electrode pair through which an electric current flows is only in the middle within a cross-section of the channel 44 (refer to FIG. 6), only the middle within the cross-section corresponds to a part to be heated, causing a temperature unevenness.

In contrast thereto, the electrode pair 21 of the present example can be provided, as depicted in FIG. 2, in a size of electrodes each having a width of about a half of the diameter of the ring channel 20. Because the electrode pair 21 can be formed in a large size, the manufacturing accuracy requirement can be reduced when forming the electrode pair 21. The reduction in manufacturing accuracy specifically means a relaxation in the alignment accuracy and a reduction in assembling labor.

Moreover, because the gap of the electrode pair 21 is across the entire width within a cross-section of the ring channel 20, the whole cross-section of a reaction solution flowing through the gap of the electrode pair 21 can be heated. Further, because there is no temperature difference in a cross-sectional direction to intersect the flow path, heating can be evenly performed without temperature unevenness, and the heating efficiency is also high. As above, in the present example, because the gap of the electrode pair 21 horizontally crosses the ring channel 20, a heating region is small, and heating power can be reduced accordingly.

Here, as described above, the present example enables downsizing the ring channel 20. Therefore, in the downsized ring channel 20, PCR amplification can be performed with a small amount of reaction solution, so that a PCR cycle can be sufficiently realized even when the heating power is smaller than that of the conventional example. That is, because the ring channel 20 is small in size, the present example enables sufficiently circulating a reaction solution even in a small amount, and enables sufficiently raising the temperature even by small heating power.

Figure 3:
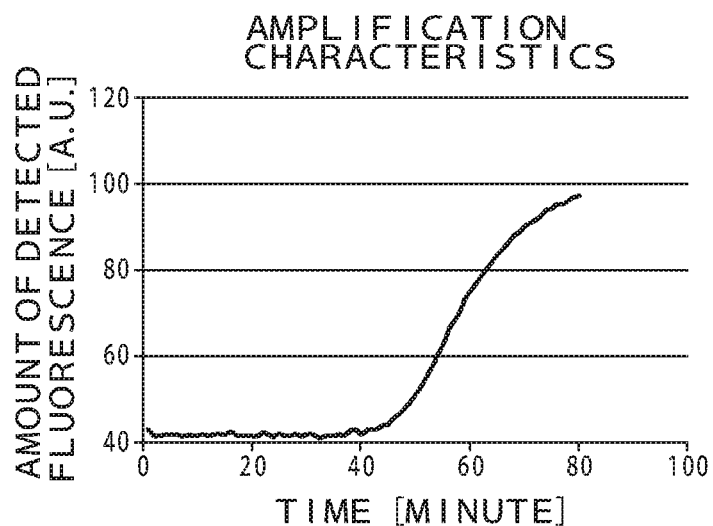
FIG. 3 is a graph showing amplification characteristics with use of the reaction container of the PCR device according to the present invention.

FIG. 3 is a graph showing amplification characteristics with use of the reaction container 10 (downsized flow path) of the PCR device 1 according to Example 1, and depicts the amount of detected fluorescence [A.U. (arbitrary unit)] at the voltage application time [minute].

The amplification characteristics (FIG. 3) were obtained by the following conditions.

Flow path volume of ring channel 20: 0.47 μL
Application voltage: 11.0V
Channel forming plate 12 (spacer) thickness: 0.3 mm
Shooting interval: 20 sec.
Master mix: illustra (GE Healthcare Corp.)
Template: λDNA 1.31 ng/25 μL
Target DNA: 199 bp Illustra by GE Healthcare Corp. was used as a master mix of polymerase and other ingredients necessary for a PCR. λDNA as a template gene, a primer for excising a specific part (target DNA) in the template gene, and EvaGreen by Biotium Inc. as a fluorescent dye for observation of gene amplification were mixed into the master mix, and prepared into a sample. A primer having a base sequence to excise (further amplify) 199 bp of target DNA from the λDNA was used as the primer.

As shown by the amplification characteristics in FIG. 3, it could be confirmed that a sufficient amount of PCR products for the voltage application time were obtained.

Moreover, while PCR amplification characteristics at a template concentration of 1.31 ng/25 μL have been shown here, it was confirmed that curves of characteristics at different template concentrations not shown here have same-shaped curves that are moved in an earlier direction (left direction in FIG. 3) at a higher concentration and in a later direction (right direction in FIG. 3) at a lower concentration. This nature is similar to that of a real-time PCR to be used for a quantitative measurement of the template concentration. According to the present example, a real-time PCR is possible.

Figure 4:
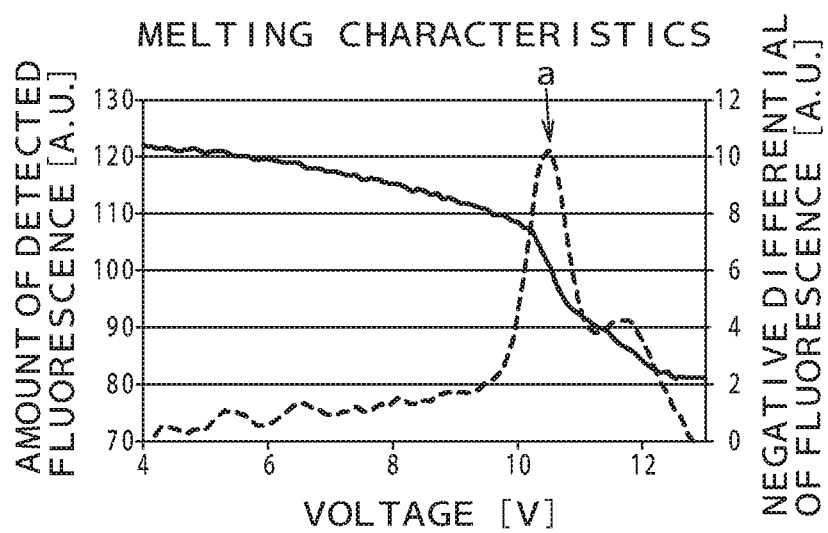
FIG. 4 is a graph showing melting characteristics with use of the reaction container of the PCR device according to the present invention.

FIG. 4 is a graph showing melting characteristics after amplification, and depicts the amount of detected fluorescence [A.U.] (solid line) and the negative differential of detected fluorescence [A.U.] (broken line) against the applied voltage [V]. After completion of amplification, the ambient temperature being an annealing/extension temperature is kept as it is, the application voltage between the electrodes is lowered, and then the application voltage is raised to raise the sample in temperature in a region near the gap between the electrodes while observing the florescent brightness of the region, whereby melting characteristics can be obtained. At that time, the sample begins to circulate again with a temperature rise of the region, but amplification has already been completed to saturation, and therefore does not further proceed, so that there is no hindrance in observing melting characteristics. Because the length of melting DNA depends on the temperature, observing melting characteristics allows verifying the presence of respective lengths of DNA. As depicted in FIG. 4, it could be confirmed that a peak (refer to the reference sign a in FIG. 4) could be obtained at a voltage corresponding to a melting temperature of the specific product (target DNA) and non-specific byproducts were not amplified. The PCR method according to the present example has an advantage that a real-time PCR is possible and electrophoresis is unnecessary to also make sample recovery unnecessary. Therefore, the outlet well 16 is not indispensable.

In the following, description will be given of technical elements of the present example.

The respective steps in a PCR cycle have minimum required times.

Generally, in a PCR, three steps of (1) denaturation step (95° C. to 98° C.), (2) annealing step (temperature is various), and (3) extension step (temperature is between the two temperatures mentioned above and is still not constant) are used. Recently, a method of two steps has been used in which the above (2) and (3) are made into a common step to be handled at the same temperature based on demand for a faster reaction, and particularly in a real-time PCR, a method of two steps called a fast PCR has been often used.

In the fast PCR, a time of 1 to 5 seconds is set for (1) denaturation step, and for the step of the above (2) and (3), a minimum time (which is said to be proportional at a rate of 1 minute per a 1 kbp length) is set according to the length of the target DNA.

In an experiment by the present inventor, it was found that a moment of time to pass through the gap between the electrodes is sufficient for (1) denaturation step. In the present example, the experiment was performed using an inner wall of 1 mmϕ and an outer wall of 2.5 to 3 mmϕ of the flow path of the ring channel 20. As a result, it has become clear that as compared with the conventional example, the speed that the reaction solution circles around the ring channel 20 is slowed to a level of approximately ⅔, but the PCR reaction is surprisingly faster than expected. This finding indicates that, even when the buoyancy being a driving source of a flow is weak, a reduction in the distance of a flow path for circulation causes falling within a range of practical use. In terms of the shape, a smaller flow path can be fabricated if it is formed by photolithography that is used in a semiconductor process, and thus there is a possibility of a faster reaction. That is, the present invention can provide an innovative advantage that a PCR is realized with a very small sample volume. Currently, in commercially-available common PCRs (including real-time PCRs), microtubes of 0.2 mL are used, and samples on the order of 20 µL to 100 µL are required. The present example requires a smaller sample, which is 0.5 µL even in the device that is currently under experimentation. Furthermore, this does not mean the smallest limit, and a further reduction in volume is possible.

Example 2

In Example 1, the electrodes 21 are provided on the substrate 11 of one side. Example 2 will be described in terms of an example for which electrodes are provided one each on a substrate and its opposite substrate to become an electrode pair.

Figure 5:
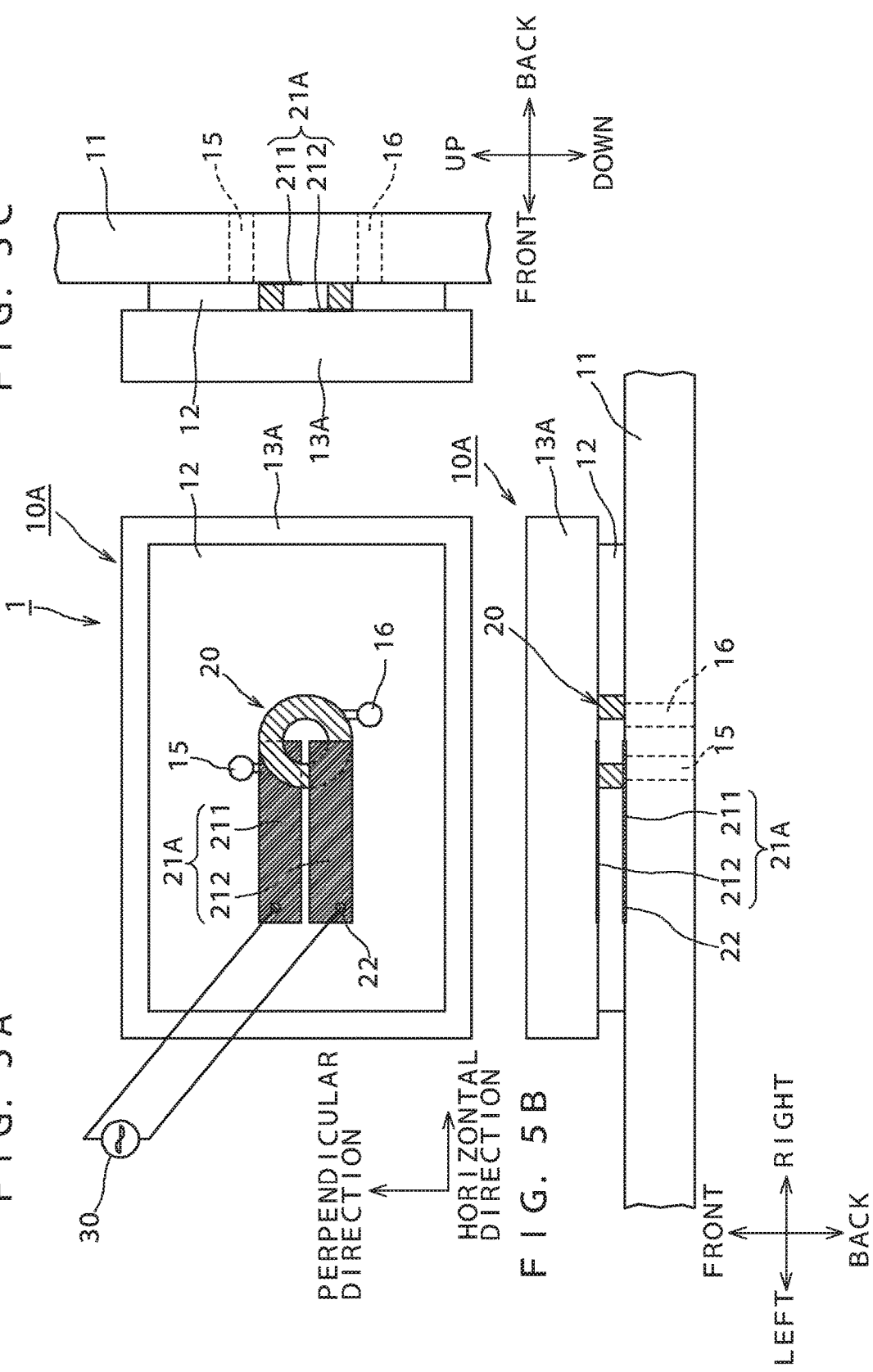
FIG. 5A to FIG. 5C are views depicting a configuration of a reaction container of a PCR device according to Example 2 of the present invention.

FIG. 5A to FIG. 5C are views depicting a configuration of a reaction container of a PCR device according to Example 1 of the present invention, FIG. 5A is its front view, FIG. 5B is its bottom view, and FIG. 5C is its side view. In the description of Example 2, components identical to those in FIG. 1A to FIG. 1C and FIG. 2 will be denoted by identical reference signs to omit description of overlapping parts.

As depicted in FIG. 5A to FIG. 5C, the reaction container 10A (annular container) of the PCR device 1 comprises a substrate 11, a channel forming plate 12, and an opposite substrate 13A, and the reaction container 10A is vertically erected. The substrate 11, the channel forming plate 12, and the opposite substrate 13A form an annular tubular ring channel 20. The opposite substrate 13A functions also as the cover plate 13 of Example 1.

The substrate 11 and the opposite substrate 13A are fixed with the channel forming plate 12 interposed therebetween. One electrode 211 of an electrode pair 21A is disposed on an inner surface of the substrate 11, and the other electrode 212 is disposed on an inner surface of the opposite substrate 13A, and the one electrode 211 and the other electrode 212 compose, with a reaction solution interposed therebetween, an electrode pair 21A that applies voltage horizontally across a cross-section in the middle of the ring channel 20. As depicted in FIG. 5C, the one electrode 211 and the other electrode 212 of the electrode pair 21A are disposed so as not to overlap each other. In addition, the two electrodes 211 and 212 being the electrode pair 21A are disposed on each of the substrates (substrate 11 and opposite substrate 13A) facing each other, and an electric current flows from the electrode 211 of the one substrate 11 to the electrode 212 of the opposite substrate 13A. Because an electric current accordingly flows from an edge of the electrode 211 to an edge of the electrode 212, that is, flows from one substrate to the other substrate, an electric current evenly flows within a flow path cross-section, allowing more even heating even when compared with that in Example 1.

A reaction solution is subjected to Joule heating by the electrode pair 21A to reach a denaturation temperature, and made into an upward flow in the periphery of the electrode pair 21A to annularly circulate within the flat ring channel 20 so as to perform a PCR cycle. A two-step PCR cycle is assumed here. The present example also uses an upward flow of the reaction solution by Joule heating.

In the case of Example 1, because electric current is made to flow along the substrate 11, a large amount of heat escapes through the substrate even after heating, but because electric current is made to flow from the substrate 11 to the opposite substrate 13A in the middle (the thickness direction) of the ring channel 20 in the case of the present example, escaping heat can be reduced to perform temperature control with efficiency. Moreover, in the case of the present example, because the distance of a gap between the electrodes is defined by a spacer being the channel forming plate 12, no expensive patterning of an electrode pair is necessary, and an electrode pair can be evenly manufactured at low cost.

However, the present invention is not limited to the above-described examples.

The material of each component is not limited to the foregoing material, and a component made of a material to be used for a common microchannel can be adopted.

Particularly in Example 1 where two electrodes are formed on the substrate 11, a description has been given of different materials of the cover plate 13 being made of glass and the channel forming plate 12 being made of PDMS, but the same material may be used for both the cover plate 13 and the channel forming plate 12. For example, in the case of PDMS being the same material, integral molding is facilitated, which is advantageous as a manufacturing method suitable for mass production.

Moreover, the "intersect (s)" is not limited to intersecting at right angles.

REFERENCE SIGNS LIST

1 PCR device
10, 10A Reaction container (annular container)
11 Substrate
12 Channel forming plate
13 Cover plate
13A Opposite substrate (cover plate)
15 Inlet well
16 Outlet well
20 Ring channel
21, 21A Electrode pair
22 Leader electrode portion
20a Circular opening portion
30 Control section (control unit)
211, 212 Electrode
G Gap width of electrode pair
GL Gap length of electrode pair
D Flow path depth of ring channel

The invention claimed is:

1. A PCR device comprising:
an annular container having a first substrate and a second substrate being opposed to the first substrate to form the annular container, the first substrate being disposed vertically, a flow path formed in the annular container having a cross-section of which is rectangular, the annular container being in a circular annular shape as a whole and being vertically oriented, to carry out polymerase chain reaction (PCR);
an electrode pair disposed on one inner surface of opposed substrates, the electrodes of the electrode pair being disposed to face each other with a gap interposed therebetween, said gap extending horizontally across an entire width of a flow of a reaction solution, intersecting the flow, and having a horizontal gap center line; and
a control unit which applies an AC voltage to the electrode pair to make an AC current flow through the reaction solution, thereby generating Joule heat to make the reaction solution flow upward, across the gap center line and each electrode of the electrode pair, and control the reaction solution in temperature.

2. A PCR device comprising:
an annular container, having a first substrate and a second substrate being opposed to the first substrate to form the annular container, the first substrate being disposed vertically, a flow path disposed within in the annular container having a cross-section which is rectangular, the annular container is in a circular annular shape as a whole and being vertically oriented, to carry out polymerase chain reaction (PCR);
an electrode pair consisting of electrodes each of which is disposed on respective inner surfaces of opposed substrates, the electrodes of the electrode pair being disposed to face each other with a gap interposed therebetween, said gap extending horizontally across an entire width of a flow of a reaction solution, intersecting the flow, and having a horizontal gap center line; and
a control unit which applies an AC voltage to the electrode pair to make an AC current flow through the reaction solution, thereby generating Joule heat to make the reaction solution flow upward, across the gap center line and each electrode of the electrode pair, and control the reaction solution in temperature.

3. A PCR method of providing an annular container, the annular container having an electrode pair consisting of two electrodes disposed on one inner surface of opposed substrates, a flow path, a cross-section of which is rectangular, and the annular container being in a circular annular shape as a whole and being vertically oriented, to carry out polymerase chain reaction (PCR), and the electrodes of the electrode pair being disposed to face each other with a gap interposed therebetween, said gap extending horizontally across an entire width of a flow of a reaction solution, intersecting the flow, and having a horizontal gap center line, and applying an AC voltage to the electrode pair to make an AC current flow through the reaction solution, thereby generating Joule heat to make the reaction solution flow upward, across the gap center line and each electrode of the electrode pair, and control the reaction solution in temperature.

4. A PCR method of providing an annular container, the annular container having an electrode pair consisting of electrodes each of which is disposed on respective inner surfaces of opposed substrates, a flow path, a cross-section of which is rectangular, and which is in a circular annular shape, vertically orienting the annular container to carry out polymerase chain reaction (PCR), and providing the electrodes of the electrode pair to be disposed to face each other with a gap interposed therebetween, said gap extending horizontally across an entire width of a flow of a reaction solution, intersecting the flow, and having a horizontal gap center line, and applying an AC voltage to the electrode pair to make an AC current flow through the reaction solution, thereby generating Joule heat to make the reaction solution flow upward, across the gap center line and each electrode of the electrode pair, and control the reaction solution in temperature.

* * * * *